United States Patent [19]
Balschmidt et al.

[11] Patent Number: 5,898,067
[45] Date of Patent: Apr. 27, 1999

[54] CRYSTALLIZATION OF PROTEINS

[75] Inventors: Per Balschmidt, Espergæde, Denmark; Jean Lesley Whittingham, York, United Kingdom

[73] Assignee: Novo Nordisk A/S, Bagsværd, Denmark

[21] Appl. No.: 09/017,085

[22] Filed: Feb. 2, 1998

Related U.S. Application Data

[60] Provisional application No. 60/038,458, Feb. 20, 1997.

[30] Foreign Application Priority Data

Feb. 7, 1997 [DK] Denmark ................................. 0140/97

[51] Int. Cl.$^6$ ............................. C07K 1/30; C07K 1/32; C07K 14/62
[52] U.S. Cl. ......................... 530/305; 530/344; 530/419; 530/420
[58] Field of Search ..................................... 530/303, 304, 530/305, 344, 345, 406, 410, 418, 419, 420, 421; 514/3, 4

[56] References Cited

U.S. PATENT DOCUMENTS

| | | | |
|---|---|---|---|
| 3,856,771 | 12/1974 | Jackson | 530/303 |
| 3,884,897 | 5/1975 | Geiger et al. | 530/303 |
| 3,907,763 | 9/1975 | Brandenburg et al. | 530/303 |
| 4,959,351 | 9/1990 | Grau | 514/4 |
| 5,008,241 | 4/1991 | Markussen et al. | 514/3 |
| 5,028,586 | 7/1991 | Balschmidt et al. | 514/3 |
| 5,461,031 | 10/1995 | De Felippis | 514/4 |
| 5,700,904 | 12/1997 | Baker et al. | 530/305 |
| 5,750,497 | 5/1998 | Havelund et al. | 514/3 |

FOREIGN PATENT DOCUMENTS

| | | |
|---|---|---|
| 0747391 A2 | 12/1996 | European Pat. Off. . |
| 2290294 | 12/1995 | United Kingdom . |

OTHER PUBLICATIONS

Whittingham et al, Crystal Structure of a Prolonged–Acting . . . Biochemistry. vol. 36, pp. 2826–2831, Mar. 11, 1997.

*Primary Examiner*—Jeffrey E. Russel
*Attorney, Agent, or Firm*—Steve T. Zelson, Esq.; Reza Green, Esq.; Valeta Gregg, Esq.

[57] ABSTRACT

A method of providing zinc containing crystals of a protein derivative which has a lysine residue which carries a lipophilic substituent on the $\epsilon$-amino group, said method comprising providing a solution of the protein derivative in an alkaline buffer, which further contains a zinc salt, adjusting the pH value of the solution to a value between 7 and 10, and isolating the crystals formed.

28 Claims, No Drawings

CRYSTALLIZATION OF PROTEINS

CROSS-REFERENCE TO RELATED APPLICATIONS

This application claims priority under 35 U.S.C. 119 of Danish application Ser. No. 0146/97 filed Feb. 7, 1997 and U.S. provisional Ser. No. 60/038,458 filed Feb. 20, 1997, the contents of which are fully incorporated herein by reference.

FIELD OF THE INVENTION

The present invention relates to a method of providing filterable crystals of zinc complexes of a protein which has a lysine residue which carries a lipophilic substituent on the ε-amino group. In particular, the present invention relates to a method of providing crystals of zinc complexes of proinsulins, insulins and insulin analogues which have a lysine residue which carries a lipophilic substituent on the ε-amino group. Optionally, the crystals also contain a phenol.

BACKGROUND OF THE INVENTION

The isolation of pharmaceutical proteins in the crystalline state is important because crystals can be dried easily and subsequently stored at low temperature under conditions where the stability of the bulk protein is optimal. Insulins and insulin analogues in which the ε-amino group of a lysine residue contained therein has a lipophilic substituent e.g. in the form of an acyl group have a protracted profile of action and show promise for use in long-acting basal therapy in the treatment of IDDM (insulin-demanding diabetes mellitus) and NIDDM (non-insulin-demanding diabetes mellitus). The preparation of such acylated insulins and insulin analogues is described in Japanese patent application 1-254,699 (Kodama), in WO 95/07931 (Novo Nordisk), in EP 0 712 862 A2 (Eli Lilly) and in WO 96/29344 (Novo Nordisk). Unfortunately, such acylated insulins and insulin analogues have been found to be less prone to crystallize than the unmodified parent compounds.

Proinsulins, insulins and insulin analogues are labile proteins and their stability depends i.a. on the purity of the particular preparation. Optimal stability can be expected when a pure preparation is kept in solid form, in particular in the form of crystals.

Unfortunately, precipitation of these compounds from solutions usually leads to amorphous precipitates which are difficult or impossible to isolate by filtration. In stead they can be isolated by centrifugation. However, when they are isolated by centrifugation it is difficult to free the particles efficiently from the mother liquor. Even when amorphous particles can be isolated by filtration, the amorphous material will usually be less pure than corresponding crystals because more impurities are embedded in amorphous material than in crystals.

The preparation of of $N^{\epsilon B29}$-(myristoyl)des(B30) human insulin is described in European patent application No. 94926816.3, Example 33. These zinc-free crystals were precipitated at pH 9 from 20% aqueous ethanol containing 0.625M sodium chloride. A method for recovering acylated proteins, especially certain fatty acid-acylated insulins, by precipitation and filtration as a freely-flowing powder is described in EP 0 747 391 A2 (Eli Lilly). According to this method a filterable precipitate of a protein is obtained by adjusting the pH of an aqueous solution containing the protein and adding a suitable amount of alcohol. For use in therapy, proteins must be prepared in highly purified form and the storage conditions must ensure that degradation during the storage is minimized. An acylated insulin or an acylated insulin analogue in highly purified form is administered in the form of a solution of a zinc complex thereof in a composition which further comprises a phenolic compound. Accordingly, it would be convenient in the production to store the bulk acylated insulin or acylated insulin analogue in the form of filterable crystals containing both insulin or insulin analogue, zinc and a phenolic compound.

It is thus an object of the present invention to provide a method by which zinc complexes of an acylated insulin or an acylated insulin analogue, optionally also containing a phenolic compound, can be obtained in filterable, crystalline form.

According to the invention this object has been accomplished by precipitating the acylated insulin or acylated insulin analogue from an aqueous buffer.

SUMMARY OF THE INVENTION

Thus, in its broadest aspect, the present invention relates to a method of providing zinc containing crystals of a protein derivative which has a lysine residue which carries a lipophilic substituent on the ε-amino group, said method comprising (a) providing a solution of the protein derivative in an alkaline buffer which further contains a zinc salt, (b) adjusting the pH value of the solution to a value between 7 and 10, and c) isolating the crystals formed.

In a preferred embodiment, the protein derivative which has a lysine residue which carries a lipophilic substituent on the ε-amino group is a proinsulin, an insulin or an insulin analogue in which the ε-amino group of a lysine residue carries an acyl group.

In another preferred embodiment, the protein derivative is an insulin derivative selected from the group comprising $N^{\epsilon B29}$-(myristoyl)des(B30) human insulin, $N^{\epsilon B29}$-(myristoyl) human insulin, $N^{\epsilon B29}$-(palmitoyl) human insulin, $N^{\epsilon B28}$-(myristoyl)LyS$^{B28}$Pro$^{B29}$ human insulin, $N^{\epsilon B28}$-(palmitoyl)LyS$^{B28}$Pro$^{B29}$ human insulin, $N^{\epsilon B30}$-(myristoyl)Thr$^{B29}$LyS$^{B30}$ human insulin, $N^{\epsilon B30}$-(palmitoyl)Thr$^{B29}$LyS$^{B30}$ human insulin, $N^{\epsilon B29}$-(N-palmitoyl-γ-glutamyl)des(B30) human insulin, $N^{\epsilon B29}$-(N-lithocholyl-γ-glutamyl)des(B30) human insulin and $N^{\epsilon B29}$-(w-carboxyheptadecanoyl)des(B30) human insulin.

In another preferred embodiment, a phenol is added to the solution before the final adjustment of the pH value.

In another preferred embodiment, an amount of phenol added which is from about 1.5% (w/w) to about 10% (w/w), preferably from about 1.5% (w/w) to about 3% (w/w) of the amount of protein present in the solution.

In another preferred embodiment, a phenol selected from the group comprising hydroxybenzene, m-cresol, methylparabene and ethylparabene is added.

In another preferred embodiment, the lipophilic group on the ε-amino group of the lysine residue is an acyl group having from 4 to 40, more preferred from 10 to 40 carbon atoms.

In another preferred embodiment, the lipophilic group on the ε-amino group of the lysine residue is a straight chain acyl group.

In further preferred embodiments, the buffer is composed of ammonia or an amine and an acid; the buffer is composed of ammonia and phosphoric acid, ammonia and a carboxylic acid, an amine and phosphoric acid, or an amine and a carboxylic acid.

In another preferred embodiment, when the buffer is composed of an amine and an acid, the amine is selected from the group comprising tris(hydroxymethyl) aminomethane, 2-amino-2-methyl-1,3-propanediol, 2-hydroxyethylamine and tris(2-hydroxyethyl)amine.

In another preferred embodiment, the buffer is composed of an ampholytic compound, preferably aspartic acid or N-tris(hydroxymethyl)methylglycine, and optionally an acid.

In another preferred embodiment, when the buffer is composed of ammonia and a carboxylic acid or an amine and a carboxylic acid, the carboxylic acid is selected from the group comprising acetic acid, citric acid, lactic acid, malic acid, malonic acid, succinic acid, tartaric acid, tartronic acid and tricarballylic acid.

In another preferred embodiment, the concentration of the ammonia or amine in the buffer is between 0.1M and 1M, preferably between 0.2M and 0.6M.

In another preferred embodiment, the concentration of the phosphoric acid or the carboxylic acid in the buffer is between 0.05M and 0.5M, preferably between 0.05M and 0.2M.

In another preferred embodiment, the zinc salt added to the solution is zinc chloride or a zinc salt of a carboxylic acid, preferably a zinc salt of one the following acids: acetic acid, citric acid, lactic acid, malic acid, malonic acid, succinic acid, tartaric acid, tartronic acid and tricarballylic acid.

In another preferred embodiment, the zinc salt is added in a molar amount which is between 33% and 150% of the molar amount of the peptide monomer.

In another preferred embodiment, wherein the protein derivative which has a lysine residue which carries a lipophilic substituent on the $\epsilon$-amino group is a proinsulin, an insulin or an insulin analogue in which the $\epsilon$-amino group of a lysine residue carries an acyl group, the pH value of the solution in which the precipitation of crystals is performed is adjusted to a value in the range from about 8.0 to about 8.5.

DETAILED DESCRIPTION OF THE INVENTION

Definitions

As used in the present text the designation "insulin" is used to designate any naturally occurring insulin. The designation "insulin analogue" is used to designate a peptide with insulin activity, formally derived from a naturally occurring insulin by exchange of one or more amino acid residues and/or deletion of one or more amino acid residues and/or addition of one or more amino acid residues. An "acylated insulin" (or insulin analogue) is an insulin (or insulin analogue) which has an acyl group in the $\epsilon$-amino group of a lysine residue contained in said insulin (or insulin analogue).

Preferred embodiments

The precipitation of the crystals according to the present method is carried out in water which optionally contains a co-solvent. When a co-solvent is used, this is preferably a water-miscible solvent e.g. an alcohol.

The operations preceding the precipitation of the crystals are preferably carried out at a temperature around ambient. After standing from about 2 hours to about 40 hours at about ambient, the reaction mixture is cooled to a temperature near 0° C. until no further precipitation of crystals occurs and the crystals are collected on a filter. If desired, the crystals can be washed with an ice-cold buffer solution corresponding to the solution from which the precipitation took place and with ice-cold ethanol.

The components of the buffer solution should preferably be less prone to form zinc complexes than insulin.

The present invention is further illustrated by the following examples which, however, are not to be construed as limiting the scope of protection as described in the appended claims. The features disclosed in the foregoing description and in the following examples may, in any combination thereof, be material for realizing the invention in diverse forms thereof.

EXAMPLES

Example 1

Preparation of crystals of $N^{\epsilon B29}$-(myristoyl)des(B30) human insulin containing zinc and phenol.

Three stock solutions a), b) and c) were used during the preparation of crystals of $N^{\epsilon B29}$-(myristoyl)des(B30) human insulin. These solutions were prepared as follows:

Stock solution a): 12.11 g of tris(hydroxymethyl) aminomethane was dissolved in 80 ml of water and the pH value of the solution was adjusted to 8.30 by means of approximately 7 ml of 5N hydrochloric acid. Water was then added to a final volume of 100 ml.

Stock solution b): 14.71 g of trisodium citrate dihydrate and 0.11 g of zinc acetate dihydrate were dissolved in water and 6.25 ml of a 3% (w/v) solution of phenol in water was added and the final volume of the solution adjusted to 100 ml.

Stock solution c): 1.471 g of trisodium citrate dihydrate and 2.422 g of tris(hydroxymethyl)aminomethane were dissolved in water and the volume of the solution adjusted to 40 ml. The pH value was adjusted to 8.1 using 5N hydrochloric acid and finally the volume was adjusted to 50 ml with water.

Crystallization of $N^{\epsilon B29}$-(myristoyl)des(B30) human insulin 1.00 g of amorphous $N^{\epsilon B29}$-(myristoyl)des(B30) human insulin powder, obtained as described in WO 95/07931, was dispersed in a mixture of 38 ml of water and 2 ml of absolute ethanol and 40 ml of stock solution a) was added with stirring. When the insulin had dissolved 20 ml of stock solution b) was added and the pH value of the mixture was adjusted to be in the range 8.1–8.2 by addition of approximately 1 ml of 5N hydrochloric acid. The mixture was left at ambient temperature with slow stirring overnight and then cooled to 4° C. The crystals formed were collected on a 50 mm filter and quickly washed with ice-cold stock solution c). After draining, the crystals were washed with 20 ml of ice-cold absolute ethanol and the drained crystals were dried in vacuo.

Example 2

Preparation of crystals of $N^{\epsilon B29}$-(myristoyl)des(B30) human insulin containing zinc and phenol.

The crystallization procedure according to Example 1 was repeated with use of 2-amino-2 methyl-1,3-propanediol in place of tris(hydroxymethyl)aminomethane.

Example 3

Preparation of crystals of $N^{\epsilon B29}$-(myristoyl)des(B30) human insulin containing zinc and phenol.

The crystallization procedure according to Example 1 was repeated with use of 2-hydroxyethylamine in place of tris (hydroxymethyl)aminomethane.

Example 4
Preparation of crystals of $N^{\epsilon B29}$-(myristoyl)des(B30) human insulin containing zinc and phenol.

The crystallization procedure according to Example 1 was repeated with use of 2-amino-2 methyl-1,3-propanediol in place of tris(hydroxymethyl)aminomethane.

Example 5
Preparation of crystals of $N^{\epsilon B29}$-(myristoyl)des(B30) human insulin containing zinc and phenol.

The crystallization procedure according to Example 1 was repeated with use of ammonia in place of tris(hydroxymethyl)aminomethane.

Example 6
Preparation of crystals of $N^{\epsilon B29}$-(myristoyl)des(B30) human insulin containing zinc and phenol.

The crystallization procedure according to Example 1 was repeated with use of tris(2-hydroxyethyl)amine in place of tris(hydroxymethyl)aminomethane.

Example 7
Preparation of crystals of $N^{\epsilon B29}$-(myristoyl)des(B30) human insulin containing zinc and phenol.

The crystallization procedure according to Example 1 was repeated with use of N-tris(hydroxymethyl)methyl-glycine in place of tris(hydroxymethyl)aminomethane.

Example 8
Preparation of crystals of $N^{\epsilon B29}$-(myristoyl)des(30) human insulin containing zinc and phenol.

The crystallization procedure according to Example 1 was repeated with use of L-aspartic acid in place of tris(hydroxymethyl)aminomethane.

Example 9
Preparation of crystals of $N^{\epsilon B29}$-(myristoyl)des(B30) human insulin containing zinc and phenol.

The crystallization procedure according to Example 1 was repeated with use of L-aspartic acid in place of both tris(hydroxymethyl)aminomethane and citric acid.

Example 10
Preparation of crystals of $N^{\epsilon B29}$-(myristoyl)des(B30) human insulin containing zinc and phenol.

The crystallization procedure according to Example 1 was repeated with use of sodium acetate in place of trisodium citrate.

Example 11
Preparation of crystals of $N^{\epsilon B29}$-(myristoyl)des(B30) human insulin containing zinc and phenol.

The crystallization procedure according to Example 1 was repeated with use of disodium tartrate in place of trisodium citrate.

Example 12
Preparation of crystals of $N^{\epsilon B29}$-(myristoyl)des(B30) human insulin containing zinc and phenol.

The crystallization procedure according to Example 1 was repeated with use of disodium succinate in place of trisodium citrate.

Example 13
Preparation of crystals of $N^{\epsilon B29}$-(myristoyl)des(B30) human insulin containing zinc and phenol.

The crystallization procedure according to Example 1 was repeated with use of disodium hydrogen phosphate in place of trisodium citrate.

Example 14
Preparation of crystals of $N^{\epsilon B29}$-(myristoyl)des(B30) human insulin containing zinc and phenol.

The crystallization procedure according to Example 1 was repeated with use of disodium malate in place of trisodium citrate.

Example 15
Preparation of crystals of $N^{\epsilon B29}$-(myristoyl)des(B30) human insulin containing zinc and phenol.

The crystallization procedure according to Example 1 was repeated with use of disodium malonate in place of trisodium citrate.

Example 16
Crystallization of $N^{\epsilon B29}$-(myristoyl)Lys$^{B28}$Pro$^{B29}$ human insulin.

The crystallization procedure according to Example 1 was repeated with use of $N^{\epsilon B28}$-(myristoyl)Lys$^{B28}$Pro$^{B29}$ human insulin in place of $N^{\epsilon B29}$-(myristoyl)des(B30) human insulin.

Example 17
Crystallization of $N^{\epsilon B29}$-(ω-carboxyheptadecanoyl)des(B30) human insulin.

The crystallization procedure according to Example 1 was repeated with use of $N^{\epsilon B29}$-(ω-carboxyheptadecanoyl)des(B30) human insulin in place of $N^{\epsilon B29}$-(myristoyl)des(B30) human insulin.

Example 18
Crystallization of $N^{\epsilon B29}$-(N-lithocholyl-γ-glutamyl)des(B30) human insulin.

The crystallization procedure according to Example 1 was repeated with use of $N^{\epsilon B29}$-(N-lithocholyl-γ-glutamyl)des(B30) human insulin in place of $N^{\epsilon B29}$-(myristoyl)des(30) human insulin.

Example 19
Crystallization of $N^{\epsilon B29}$-(myristoyl)des(B30) human insulin The crystallization method according to Example 1 was performed with use of sodium chloride in place of tris(hydroxymethyl)aminomethane following the procedure described below.

Two stock solutions d) and e) were used during the crystallization procedure.

These solutions were prepared as follows:

Stock solution d): 14.71 g of trisodium citrate dihydrate, 5.844 g of sodium chloride and 0.11 g of zinc acetate dihydrate were dissolved in about 75 ml of water and after addition of 6.25 ml of a 3% (w/v) solution of phenol in water the pH value was adjusted to 8.1 using 2N sodium hydroxide and the final volume of the solution was adjusted to 100 ml.

Stock solution e): 1.471 g of trisodium citrate dihydrate and 2.922 g of sodium chloride were dissolved in about 35 ml of water. The pH value was adjusted to 8.1 using 2N sodium hydroxide and finally the volume was adjusted to 50 ml with water.

Crystallization procedure:

1.00 g of amorphous $N^{\epsilon B29}$-(myristoyl)des(B30) human insulin powder was dispersed in a mixture of 78 ml of water and 2 ml of absolute ethanol and pH was adjusted to 8.3 with 0.1M NaOH. When the insulin had dissolved 20 ml of a stock solution d) was added and the pH value of the mixture was adjusted to be in the range 8.1–8.2 by addition of 1N hydrochloric acid. The mixture was slowly stirred overnight at ambient temperature and then cooled to 4° C. The crystals formed were collected on a 50 mm planar filter and quickly washed with ice-cold stock solution e). After draining, the crystals were washed with 20 ml of ice-cold absolute ethanol and the drained crystals were dried in vacuo.

We claim:

1. A method of providing zinc-containing crystals of a protein derivative, said protein derivative having a lysine residue comprising a lipophilic substituent on the ε-amino group, said method comprising:

(a) providing a solution of the protein derivative in an alkaline buffer, said solution further containing a zinc salt;

(b) adjusting the pH value of the solution to a value between 7 and 10, wherein crystals are formed; and (c) isolating the crystals.

2. The method of claim 1, wherein the protein derivative is proinsulin, insulin or an insulin analogue, wherein the ε-amino group of a lysine residue carries an acyl group.

3. The method of claim 1 wherein the protein derivative is an insulin derivative selected from the group consisting of $N^{\epsilon B29}$-(myristoyl)des(B30) human insulin, $N^{\epsilon B29}$(myristoyl) human insulin, $N^{\epsilon B29}$-(palmitoyl) human insulin, $N^{\epsilon B28}$-(myristoyl)Lys$^{B28}$Pro$^{B29}$ human insulin, $N^{B28}$-(palmitoyl)LyS$^{B28}$Pro$^{B29}$ human insulin, $N^{\epsilon B30}$-(myristoyl)Thr$^{B29}$LyS$^{B30}$human insulin, $N^{\epsilon B30}$-(palmitoyl)Thr$^{B29}$Lys$^{B30}$human insulin, $N^{\epsilon B29}$-(N-palmitoyl-γ-glutamyl)des(B30) human insulin, $N^{\epsilon B29}$-(N-lithocholyl-γ-glutamyl)des(B30) human insulin and $N^{\epsilon B29}$-(ω-carboxyheptadecanoyl)des(B30) human insulin.

4. The method of claim 1 wherein a phenol is added to the solution prior to pH adjustment in step (b).

5. The method of claim 4 wherein the amount of phenol added is from about 1.5% (w/w) to about 10% (w/w) of the amount of protein derivative present in the solution.

6. The method of claim 4 wherein the phenol is selected from the group consisting of hydroxybenzene, m-cresol, methylparabene and ethylparabene.

7. The method of claim 1 wherein the lipophilic substituent is an acyl group having from 4 to 40 carbon atoms.

8. The method of claim 1 wherein the lipophilic substituent is a straight chain acyl group.

9. The method of claim 1 wherein the alkaline buffer is a nitrogen-containing buffer.

10. The method of claim 9 wherein the buffer is composed of ammonia or an amine and an acid.

11. The method of claim 9 wherein the buffer is composed of ammonia and phosphoric acid.

12. The method of claim 9 wherein the buffer is composed of ammonia and a carboxylic acid.

13. The method of claim 9 wherein the buffer is composed of an amine and phosphoric acid.

14. The method of claim 9 wherein the buffer is composed of an amine and a carboxylic acid.

15. The method of claim 9, wherein the buffer is composed of an ampholytic compound and optionally an acid.

16. The method of claim 13, wherein the amine is selected from the group consisting of tris(hydroxymethyl) aminomethane, 2-amino-2-methyl-1,3-propanediol, 2-hydroxyethylamine and tris(2-hydroxyethyl)amine.

17. The method of claim 12, wherein the carboxylic acid is selected from the group consisting of acetic acid, citric acid, lactic acid, malic acid, malonic acid, succinic acid, tartaric acid, tartronic acid and tricarballylic acid.

18. The method of claim 10, wherein the concentration of the ammonia or amine in the buffer is between 0.1M and 1M.

19. The method of claim 10 wherein the concentration of the acid in the buffer is between 0.05M and 0.5M.

20. The method of claim 1 wherein the zinc salt added to the solution is zinc chloride or a zinc salt of a carboxylic acid.

21. The method of claim 1 wherein the zinc salt is added in a molar amount which is between 33% and 150% of the molar amount of the protein derivative.

22. The method of claim 1 wherein the pH value is adjusted to a value in the range from about 8.0 to about 8.5.

23. The method of claim 5, wherein the amount of phenol added is from about 1.5% (w/w) to about 3% (w/w) of the amount of protein derivative present in the solution.

24. The method of claim 7 wherein the lipophilic substituent is an acyl group having from 10 to 40 carbon atoms.

25. The method of claim 15, wherein the ampholytic compound is selected from the group consisting of aspartic acid and N-tris(hydroxymethyl)methylglycine.

26. The method of claim 18, wherein the concentration of the ammonia or amine in the buffer is between 0.2M and 0.6M.

27. The method of claim 19, wherein the concentration of the acid is between 0.05M and 0.2M.

28. The method of claim 20, wherein the carboxylic acid is selected from the group consisting of acetic acid, citric acid, lactic acid, malic acid, malonic acid, succinic acid, tartaric acid, tartronic acid and tricarballylic acid.

* * * * *